(12) United States Patent
Tanaka et al.

(10) Patent No.: US 7,608,086 B2
(45) Date of Patent: Oct. 27, 2009

(54) ANASTOMOSIS WIRE RING DEVICE

(75) Inventors: Don A. Tanaka, Saratoga, CA (US);
Mark S. Ortiz, Milford, OH (US);
Darrel Powell, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 491 days.

(21) Appl. No.: 10/674,371

(22) Filed: Sep. 30, 2003

(65) Prior Publication Data

US 2005/0070934 A1 Mar. 31, 2005

(51) Int. Cl.
*A61B 17/08* (2006.01)
*A61F 2/06* (2006.01)

(52) U.S. Cl. .................. 606/153; 606/213; 623/1.51

(58) Field of Classification Search .......... 606/213, 606/154, 153, 155; 623/1.3, 1.31, 1.51
See application file for complete search history.

(56) References Cited

U.S. PATENT DOCUMENTS

| 5,720,776 | A | | 2/1998 | Chuter et al. |
| 5,725,552 | A | | 3/1998 | Amplatz et al. |
| 6,004,347 | A | * | 12/1999 | McNamara et al. ...... 623/23.64 |
| 6,007,544 | A | | 12/1999 | Kim |
| 6,355,052 | B1 | * | 3/2002 | Neuss et al. ............. 606/213 |
| 6,537,299 | B1 | | 3/2003 | Hogendijk et al. |
| 6,543,456 | B1 | | 4/2003 | Freeman |
| 6,673,084 | B1 | * | 1/2004 | Peterson et al. .......... 606/153 |
| 2002/0142119 | A1 | | 10/2002 | Seward et al. |
| 2003/0032967 | A1 | | 2/2003 | Park et al. |
| 2003/0120292 | A1 | * | 6/2003 | Park et al. ................ 606/153 |
| 2005/0070921 | A1 | | 3/2005 | Ortiz et al. |
| 2005/0070926 | A1 | | 3/2005 | Ortiz |
| 2005/0070935 | A1 | | 3/2005 | Ortiz |
| 2005/0070939 | A1 | | 3/2005 | Beaupre |

OTHER PUBLICATIONS

EPO Search Report, Serial No. EP 04 25 6019, Mar. 16, 2005, pp. 1-5.
EPO Search Report, Serial No. EP 04 25 6019, Jul. 6, 2006, pp. 1-5.

* cited by examiner

*Primary Examiner*—Tan-Uyen T. Ho
*Assistant Examiner*—Melissa Ryckman
(74) *Attorney, Agent, or Firm*—Dean Garner

(57) ABSTRACT

An anastomotic ring device for forming a hollow rivet (ring) attachment between tissue lumens facilitates laparoscopic or endoscopic implantation by including features that facilitate actuation from a stressed, generally cylindrical shape. Economical manufacturer is achieved by weaving open ended strands into a generally cylindrical stent shape that is imparted with a Shape Memory Effect (SME) to actuate to a hollow rivet (ring) shape. Alternatively or in addition to SME inherent in the woven strands, an actuating force may be received from a helical spring element incorporated into the ring. Self-actuating ring devices are enhanced by forming woven strands into petals that diverge from opposing petals such that the strands encounter less friction when actuating. Each of these features alone or in combination enhance clinical use of anastomotic ring devices, such as a bariatric gastric bypass procedure.

8 Claims, 21 Drawing Sheets

ANASTOMOSIS WIRE RING DEVICE

CROSS REFERENCE TO RELATED APPLICATIONS

The present application is related to four co-pending and commonly-owned application filed on even date herewith, the disclosure of each is hereby incorporated by reference in its entirety:

"Applier For Fastener For Single Lumen Access Anastomosis", Ser. No. 10/675,077 to Mark Ortiz, now U.S. Pat. No. 7,452,363;

"Unfolding Anastomosis Ring Device", Ser. No. 10/675,091 to Jean Beaupre, now abandoned;

"Single Lumen Access Deployable Ring for Intralumenal Anastomosis", Ser. No. 10/675,705 to Mark Ortiz, now abandoned; and "Single Lumen Anastomosis Applier for Self-Deploying Fastener", Ser. No. 10/675,497 to Mark Ortiz, Robert McKenna, Bill Kraimer, Mike Stokes, and Foster Stulen, now U.S. Pat. No. 7,309,341.

FIELD OF THE INVENTION

The present invention relates, in general, to surgery and, more particularly, to a method of performing a surgical procedure on the digestive system.

BACKGROUND OF THE INVENTION

The percentage of the world population suffering from morbid obesity is steadily increasing. Severely obese persons are susceptible to increased risk of heart disease, stroke, diabetes, pulmonary disease, and accidents. Because of the effect of morbid obesity to the life of the patient, methods of treating morbid obesity are being researched.

Numerous non-operative therapies for morbid obesity have been tried with virtually no permanent success. Dietary counseling, behavior modification, wiring a patient's jaws shut, and pharmacologic methods have all been tried, and though temporarily effective, failed to correct the condition. Further, introducing an object in the stomach, such as an esophagogastric balloon, to fill the stomach have also been used to treat the condition; however, such approaches tend to cause irritation to the stomach and are not effective long-term.

Surgical treatments of morbid obesity have been increasingly used with greater success. These approaches may be generalized as those that reduce the effective size of the stomach, limiting the amount of food intake, and those that create malabsorption of the food that it is eaten. For instance, some patients benefit from adjustable gastric bands (AGB) that are advantageously laparoscopically placed about the stomach to form a stoma of a desired size that allows food to fill an upper portion of the stomach, causing a feeling of satiety. To allow adjustment of the size of the stoma after implantation, a fluid conduit communicates between an inwardly presented fluid bladder of the AGB to a fluid injection port subcutaneously placed in front of the patient's sternum. A syringe needle may then inject or withdraw fluid as desired to adjust the AGB.

Although an effective approach to obesity for some, other patients may find the lifestyle changes undesirable, necessitated by the restricted amount of food intake. In addition, the medical condition of the patient may suggest the need for a more permanent solution. To that end, surgical approaches have been used to alter the portions of the stomach and/or small intestine available for digesting food. Current methods of performing a laparoscopic anastomoses for a gastric bypass include stapling, suturing, and placing biofragmentable rings, each having significant challenges. For instance, suturing is time consuming, as well as being technique and dexterity dependent. Stapling requires placement of an anvil, which is a large device that cannot be introduced through a trocar port. Having to introduce the port through a laparotomy presents an increased incidence of wound site infection associated with intralumenal content being dragged to the laparotomy entry site.

As an example of the latter approach, in U.S. Pat. No. 6,543,456 a method for gastric bypass surgery includes the insertion of proximal and distal anastomosis members (e.g., anvils) transorally with grasping forceps. The stomach and the small intestine are transected endoscopically by a surgical severing and stapling instrument to create a gastric pouch, a drainage loop, and a Roux limb. An endoscopically inserted circular stapler attaches to the distal anastomosis member to join the drainage loop to a distal portion of the intestine, and the circular stapler attaches to the proximal anastomosis member to join the Roux limb to the gastric pouch. Thereafter, the anastomosis members are removed to create an orifice between joined portions of the stomach and intestine. This method reduces the number of laparoscopic ports, avoids a laparoscopic insertion of an anastomosis instrument (e.g., circular stapler) into an enlarged surgical port, and eliminates the need for an enterotomy and an enterotomy closure.

While methods such as that described are a marked improvement over generally known gastric bypass and similar surgical treatments for morbid obesity, it would be desirable to achieve a gastric bypass with yet fewer procedural steps and with fewer laparoscopic insertions. Such an approach is described in U.S. Pat. Appl. Publ. No. US 2003/0032967 to Park et al., wherein gastrointestinal or enteric (including biliary) anastomosis is achieved by insertion of a sheath that perforates the walls of two tissue passages, such as the stomach and small intestine. A three-dimensional woven tube of wire of having a thermal shape memory effect (SME) ("generally-known nitinol ring device") is presented by a cannula of the sheath on both sides of the openings. Deployment of the woven tube causes the outer loops or ends of the tube to fold or loop back to hold the lumenal interface of the anastomosis site in apposition. Thereby, the need for a mechanical compression component in a delivery system is reduced or avoided, reducing the size and complexity of the delivery device.

While the generally-known nitinol ring device is a significant advancement in the treatment of morbid obesity, it is believed that further improvements would be desirable. For instance, the continuous interlocking petals are difficult to manufacturer, especially since the depicted woven tube is of a continuous wire loop bent into a pattern of interlocking triangles.

In addition, the generally-known nitinol ring device is a woven tube, or stent, that is purported to be a self-actuating anastomotic ring. However, the disclosed stent sometimes will not actuate or transform completely from its stressed cylindrical state to its relaxed clamping state, perhaps due to irregularities in undulations of its weaved designs create friction. One particular difficulty of known SME anastomotic rings are that they are designed to move from a generally cylindrical shape to a hollow rivet shape ("ring shape") by having wires that form the device move across one another. In particular, wires must move within a nodal point (i.e., an indentation or valley) created by the wire bend and must climb back out of the indentation. In some instances, the device fails to fully actuate on its own due to these sources of friction.

Consequently, there is a general need for an approach to anastomosis that will use existing trocar ports (e.g., 12 mm size) with a minimum of suturing. Moreover, aspects of the method should have application to endoscopic surgery. To that end, a significant need exists for an anastomosis device that reliably and effectively deploys and actuates to eliminate the need for surgical stapling and suturing to form an anastomosis.

BRIEF SUMMARY OF THE INVENTION

The invention overcomes the above-noted and other deficiencies of the prior art by providing an anastomosis device woven from one or more strands with end disconnected from other ends, providing a more economical manufacture.

In one aspect of the invention, a woven tube anastomotic device has each longitudinal end of its constituent strands terminate in circumferential petals. The unactuated position of the tube is of a generally cylindrical shape and the actuated position of a hollow rivet shape for insertion through and for forming an anastomotic attachment between two proximate tissue walls, respectively. An actuation force is provided by weaving a helical coil spring into the woven tube. Thereby, enhanced actuation force may be achieved without relying solely or at all upon the rest of the woven tube.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
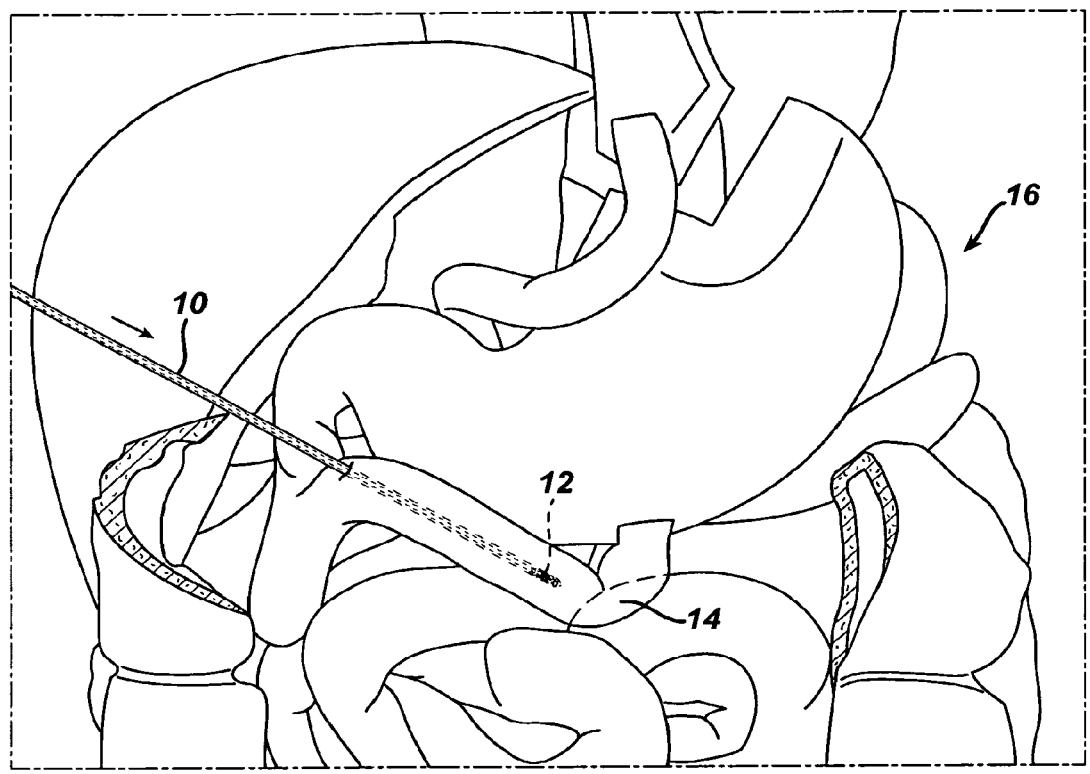
FIG. 1 is perspective view of an applier having an anastomotic ring device installed thereon being inserted laparoscopically to an anastomosis target site on each of two portions of a patient's small intestine.

Turning to the Drawings, wherein like numerals denote like components throughout the several views, FIG. 1 depicts an applier 10 that advantageously laparoscopically or endoscopically deploys and actuates an anastomotic ring device 12 from a generally cylindrical shape to one having properties of a hollow rivet, or ring, capable of forming an astomotic attachment at an anastomosis target site, such as in a bariatric gastric bypass of a morbidly obese patient 16. In the illustrative version, the anastomotic ring device 12 comprises a shape memory effect (SME) material such as nitinol that further assists in actuation to an engaging hollow rivet shape. As will be described in greater detail below, various improvements to the configuration of the anastomotic ring device 12 simplify manufacturer as well as adding therapeutic features. Moreover, configuration improvements further assist in actuating the anastomotic ring device 12 without wholly relying upon SME properties of the anastomotic ring device 12.

It will be appreciated that the terms "proximal" and "distal" are used herein with reference to a clinician gripping a handle of the applier 10. It will be further appreciated that for convenience and clarity, spatial terms such as "right", "left", "vertical" and "horizontal" are used herein with respect to the drawings. However, surgical instruments are used in many orientations and positions, and these terms are not intended to be limiting and absolute. In addition, aspects of the invention have application to surgical procedures performed endoscopically and laparoscopically, as well as an open procedure. Use herein of one of these or similar terms should not be construed to limit the present invention for use in only one category of surgical procedure.

Anastomotic Ring Device Applier.

Figure 2:
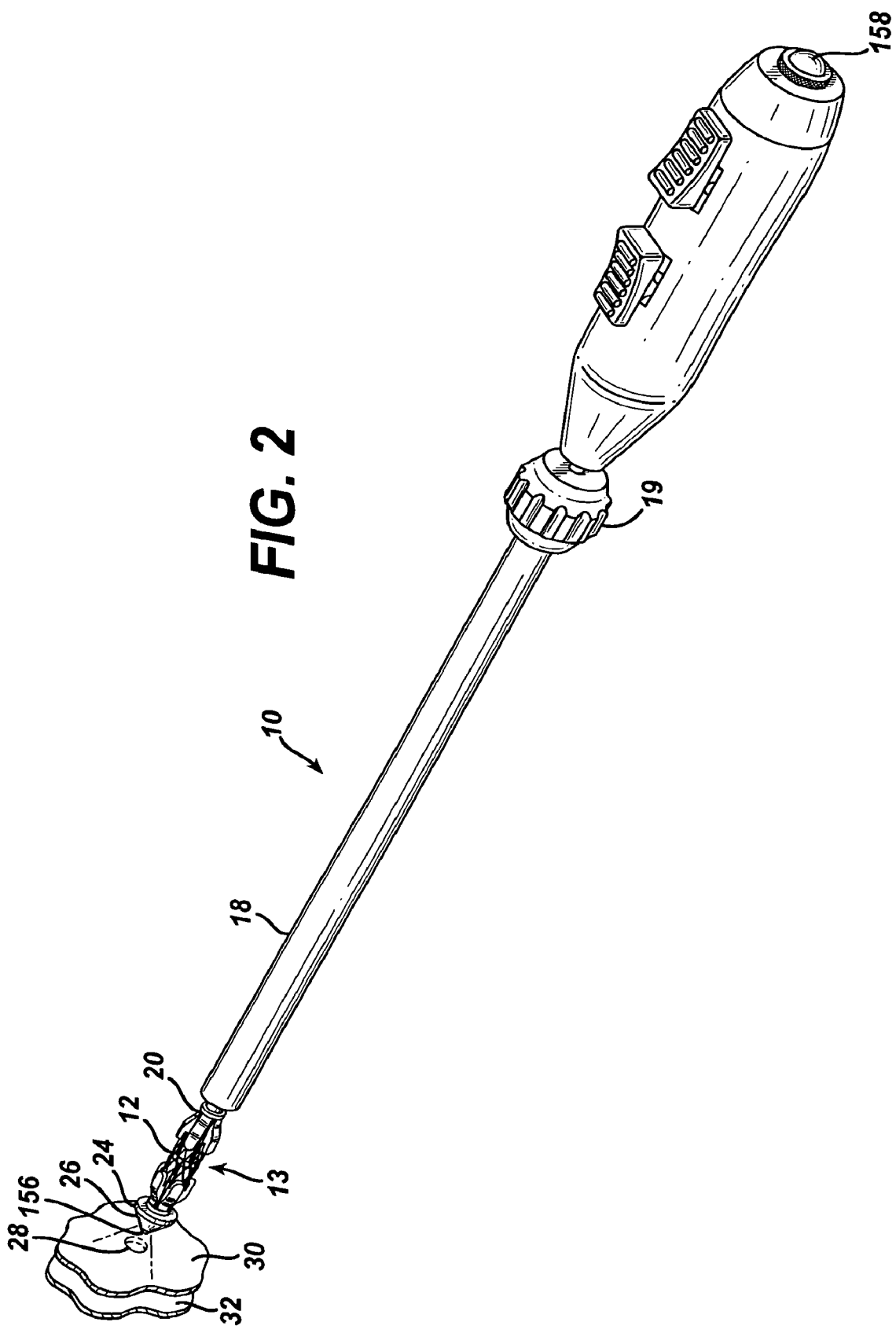
FIG. 2 is a perspective detail view of the applier with sheath retracted and anastomosis target site of FIG. 1, depicting the anastomotic ring device in its undeployed, unactuated state.
Figure 3:
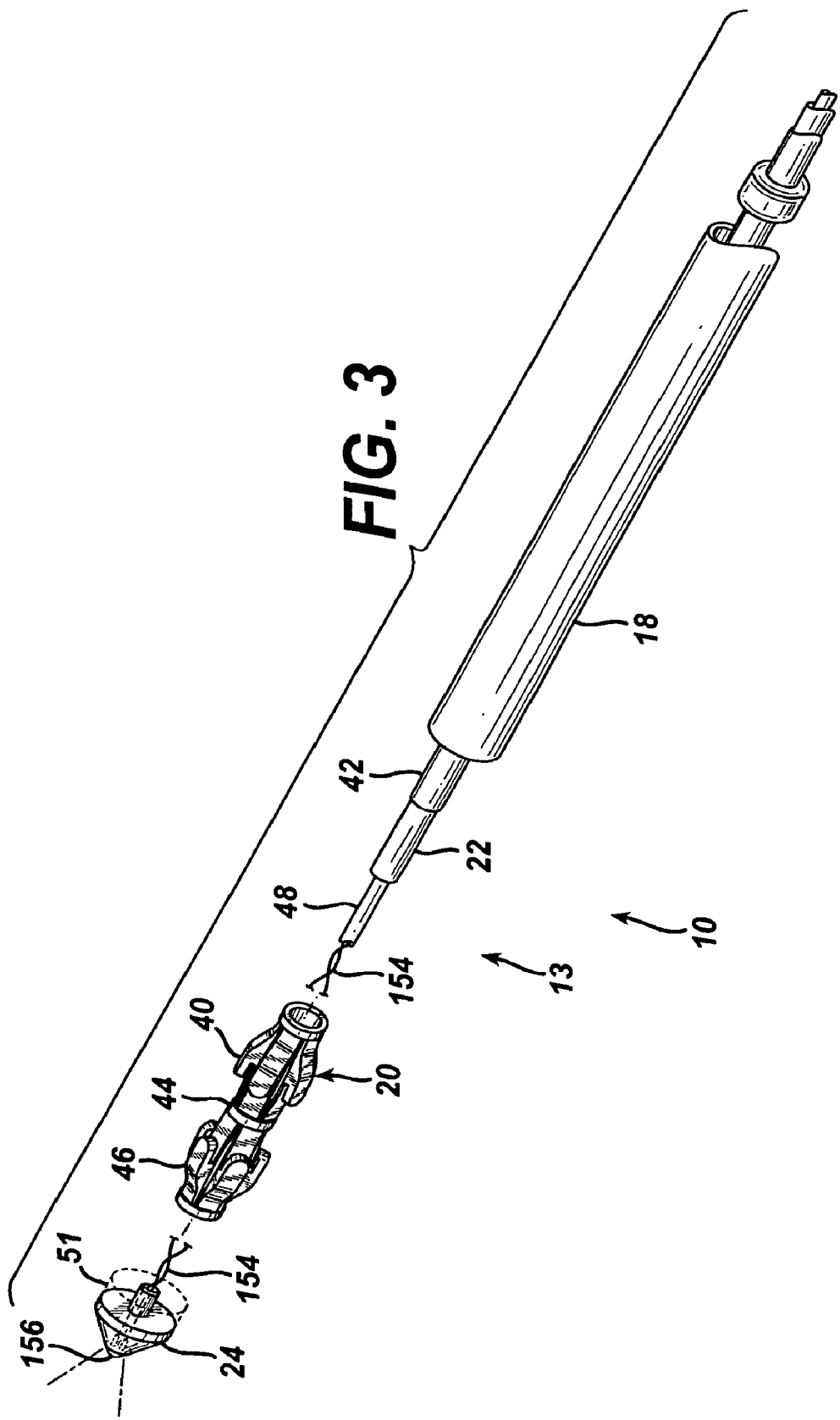
FIG. 3 is a perspective, exploded and partially cutaway view of a distal portion of the applier of FIG. 1.

In FIG. 2, the applier 10 has the anastomotic ring device 12 advantageously retained in a generally cylindrical shape distal to an outer tube 18 upon a molded actuation member 20 forming a cannula 22 that distally terminates in a tapered tip 24. This tapered tip 24 presents a distal piercing surface 26 to form an anastomotic opening 28 through apposite tissue walls 30, 32 of two gastrointestinal passages. As discussed below, the tapered tip 24 may advantageously include illumination features that allow confirmation of placement and actuation of the anastomotic ring device 12 when viewed from a proximal direction through translucent tissue walls 30, 32.

With reference to FIGS. 2-5, a handle 34, proximal to the cannula 22, includes a pair of longitudinally aligned triggers 36, 38. The proximal trigger 36, shown at its most proximal, unfired position, is coupled to proximal leaves 40 of the molded actuation member 20 via an intermediate tube 42 of the cannula 22. Distal movement of the proximal trigger 36 thus causes longitudinal distal movement of the intermediate tube 42 and proximal leaves 40, which outwardly actuate like an umbrella by a hinged relationship to a central portion 44 of the molded actuation member 20. Similarly, the distal trigger 28, shown at its most distal, unfired position, is coupled to distal leaves 46 of the molded actuation member 20 via an internal rod 48 that is coupled for movement within the intermediate tube 42. Proximal movement of the distal trigger 38 causes longitudinal proximal movement of the rod 48 and distal leaves 50 of the molded actuation member 20, which outwardly actuate by a hinged relationship to the central portion 44.

Figure 4:
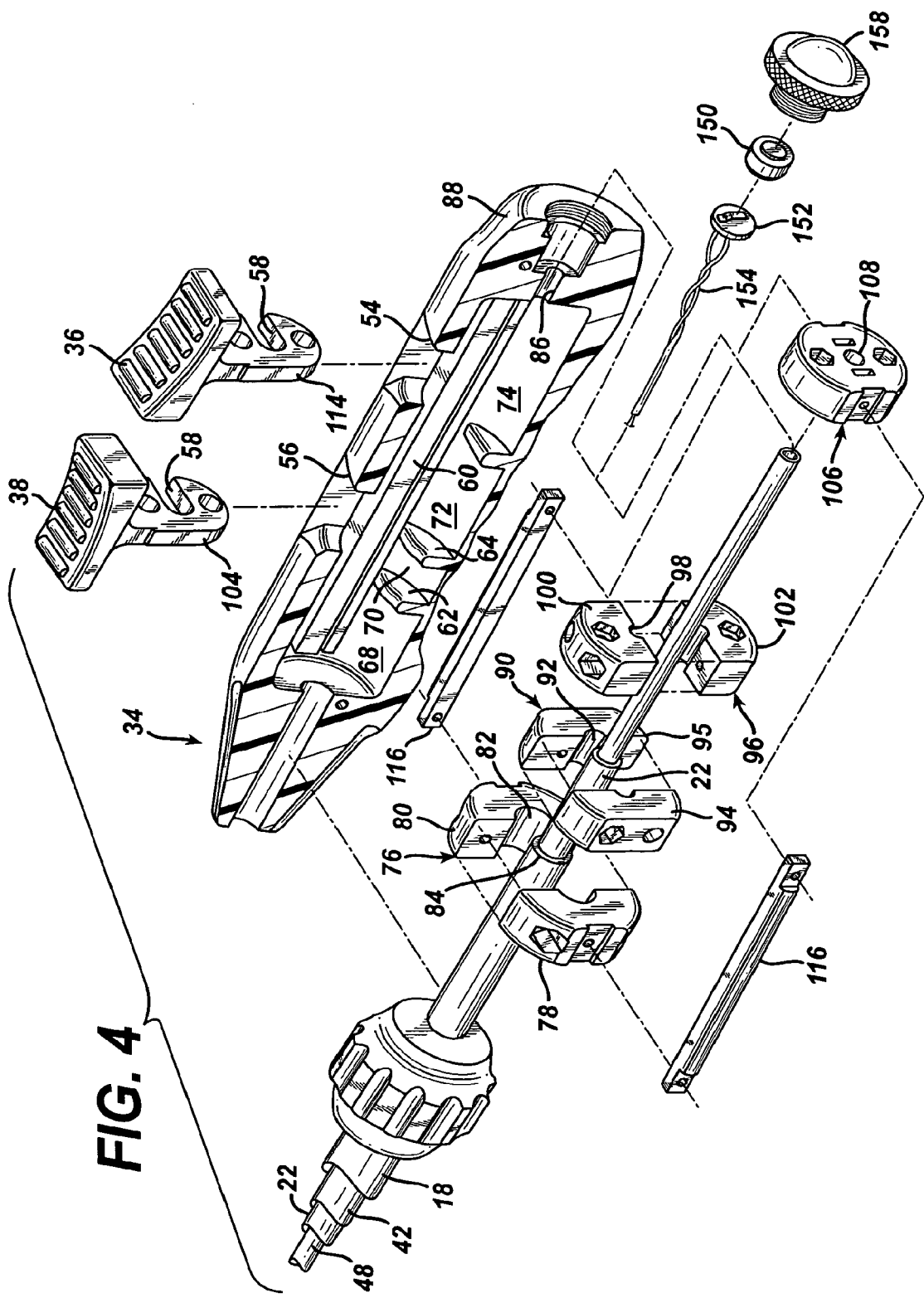
FIG. 4 is a perspective, exploded view of a proximal portion of the applier of FIG. 1 with a left housing half omitted.
Figure 5:
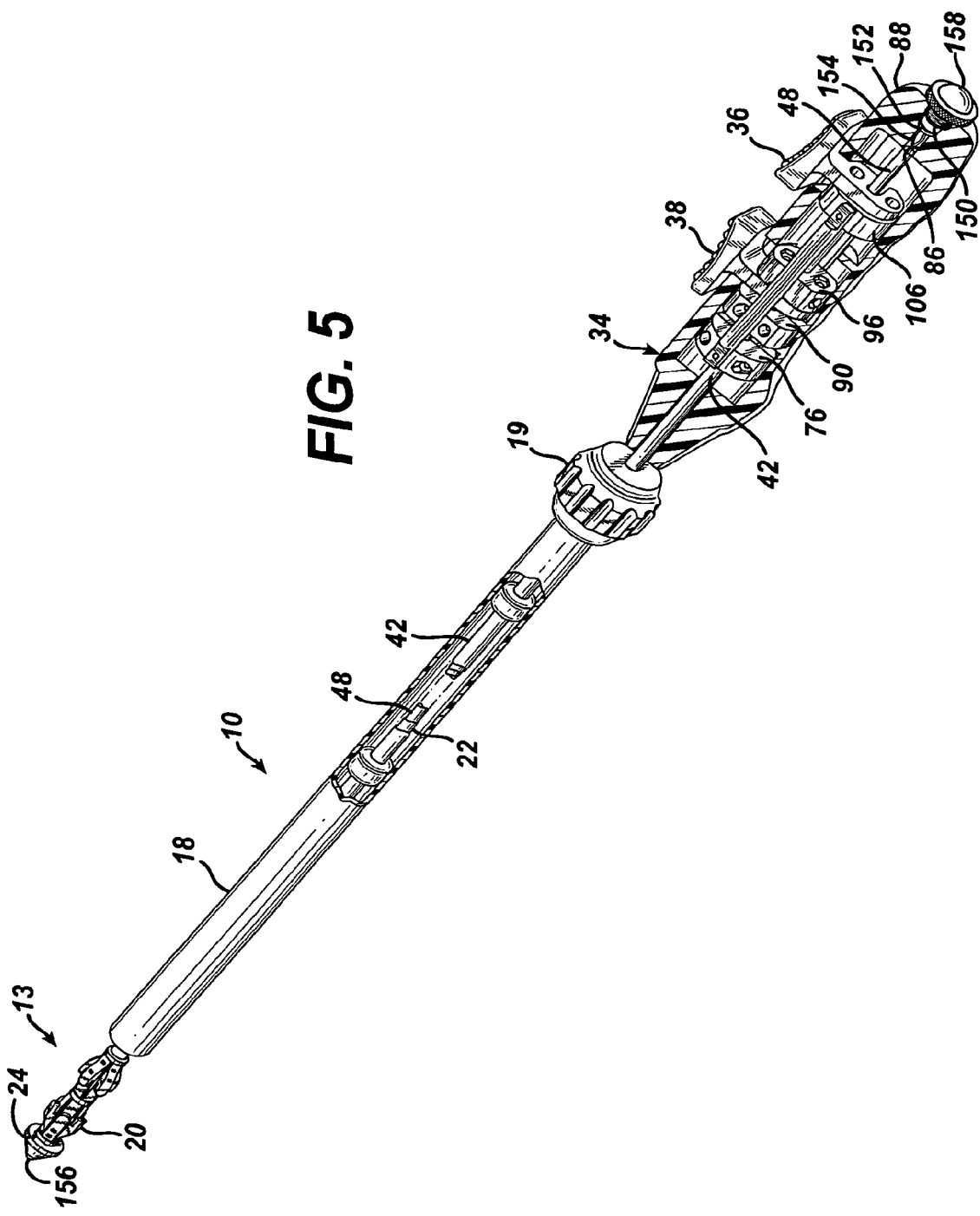
FIG. 5 is perspective view of the applier of FIG. 1 with the left housing half omitted and an outer tube of the cannula partially cutaway to expose an intermediate tube and inner rod that actuate a molded actuating member that actuates the omitted anastomotic ring device, also to expose a deployment illuminator that allows confirming actuation of an anastomotic ring device by viewing through the translucent tissue walls.

As best viewed in FIGS. 4-5, within the handle 34, a cavity 52 includes proximal and distal apertures 54, 56 to allow the longitudinal movement of the proximal and distal triggers 36, 38 respectively. Each trigger 36, 38 includes a right opening aperture 58 that engage for longitudinal movement a leftward projecting track 60 formed within the cavity 52 of a right half shell of the handle 34.

Moving from most distal to most proximal, a first, second and third lateral ridge 62, 64, 66 across the bottom of the cavity 52 define a first, second, third, and fourth cavity segment 68, 70, 72, 74 respectively. A first block 76, formed from left and right halves 78, 80 is positioned for movement within the first cavity segment 68. A longitudinal central hole 82 defined between the two halves 78, 80 engages and moves with a terminating proximal end 84 of the intermediate tube 42. The internal rod 48 passes on through the first block 76 into the second, third and fourth cavity segments 70-74 into sliding contact with a hole 86 passing through a proximal end 88 of the handle 34. A second spacer block 90 locked within the second cavity segment 70 has a longitudinal central hole 92 defined between its left and right halves 94, 95 that slidingly contacts and support the internal rod 48. A third sliding block 96 has a longitudinal central hole 98 defined between its upper and lower halves 100, 102 that engage and move with the internal rod 48. A lower portion 104 of the distal trigger 38 is attached to a distal face of the third sliding block 96. A fourth sliding block 106 within the fourth cavity segment 74 has a longitudinal central hole 108 that slidingly contacts the internal rod 48. A lower portion 114 of the proximal trigger 36 is attached to a proximal face of the fourth sliding block 106. A link 116 is attached to the left sides of the first and fourth sliding blocks 76, 106.

Figure 6:
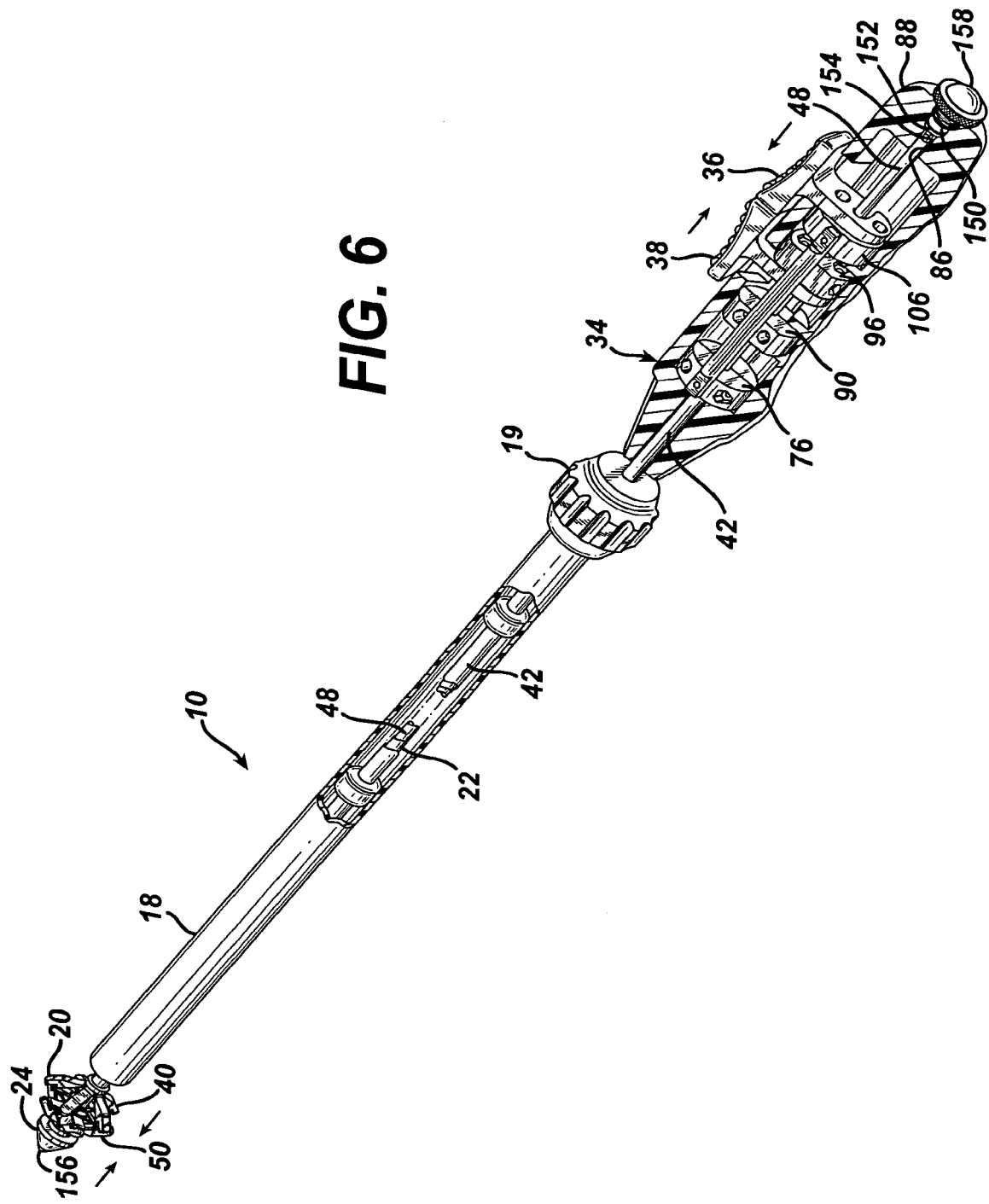
FIG. 6 is a perspective view of the applier of FIG. 5 with the triggers and molded actuating member in an actuated position.

In FIG. 6, the triggers 36, 38 have been slid toward one another to actuate the molded actuating member 20. Specifically, the distal trigger 38 has been moved proximally, moving the third sliding block 96 and internal rod 48, the distal terminating end of the latter being attached to tapered tip 24. The tapered tip thus moves toward the distal end of the intermediate tube 42. The proximal trigger 36 has been moved distally, moving fourth sliding block 106, link 116, first sliding block 76, and intermediate tube 42 also distally. The molded actuating member 20 is compressed between the inwardly moving tapered tip 24 and intermediate tube 42. The distal leaves 50 actuate lateral to the longitudinal axis, and move toward and interdigitate with the proximal leaves 40. This movement expedites actuating of an anastomotic ring device (not shown in FIG. 6).

Figure 8:
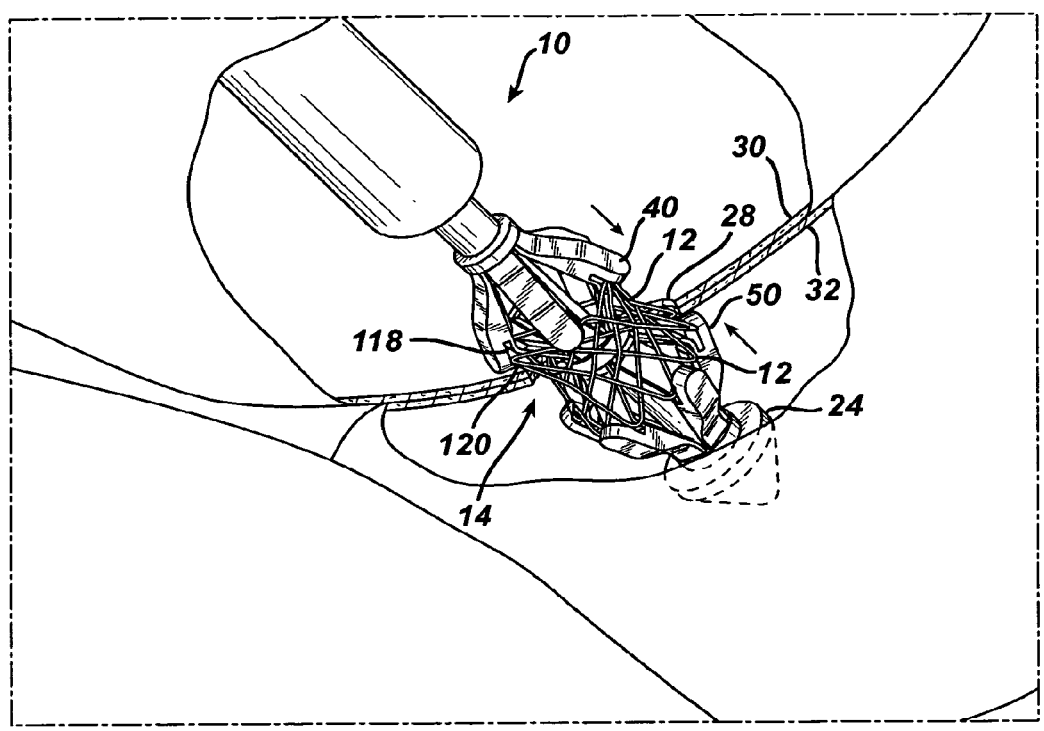
FIG. 8 is a detail perspective view of a distal portion of the applier of FIG. 7 with tissue walls partially cutaway.
Figure 9:
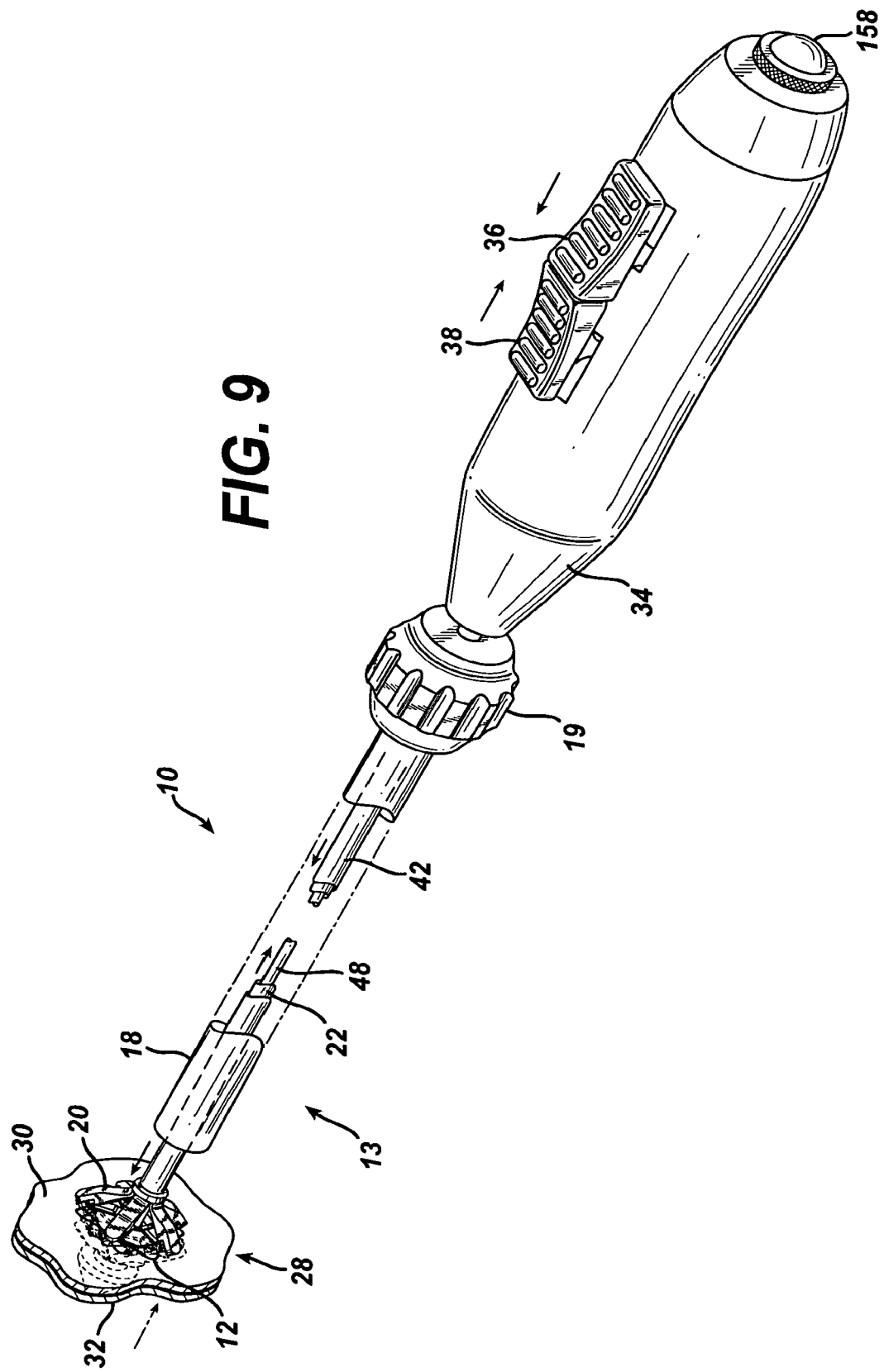
FIG. 9 is a perspective view of the applier of FIG. 1 in a fully actuated state.
Figure 10:
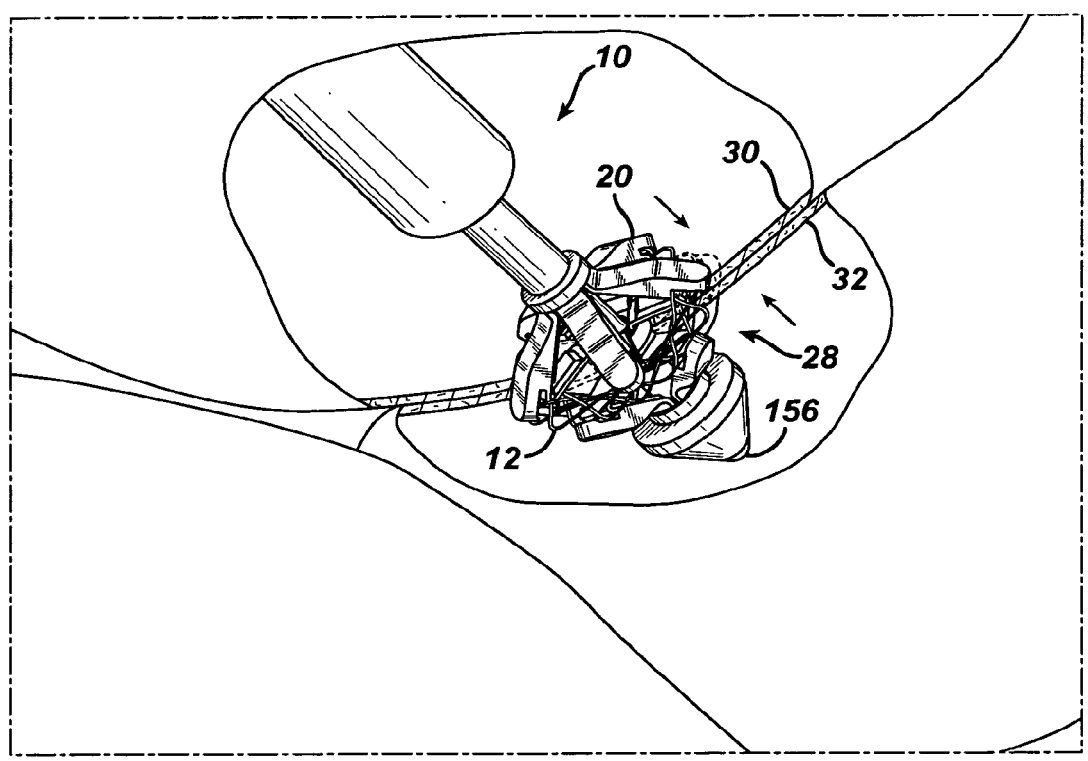
FIG. 10 is a detail perspective view of the distal portion of the applier of FIG. 9 with tissue walls partially cutaway.
Figure 11:
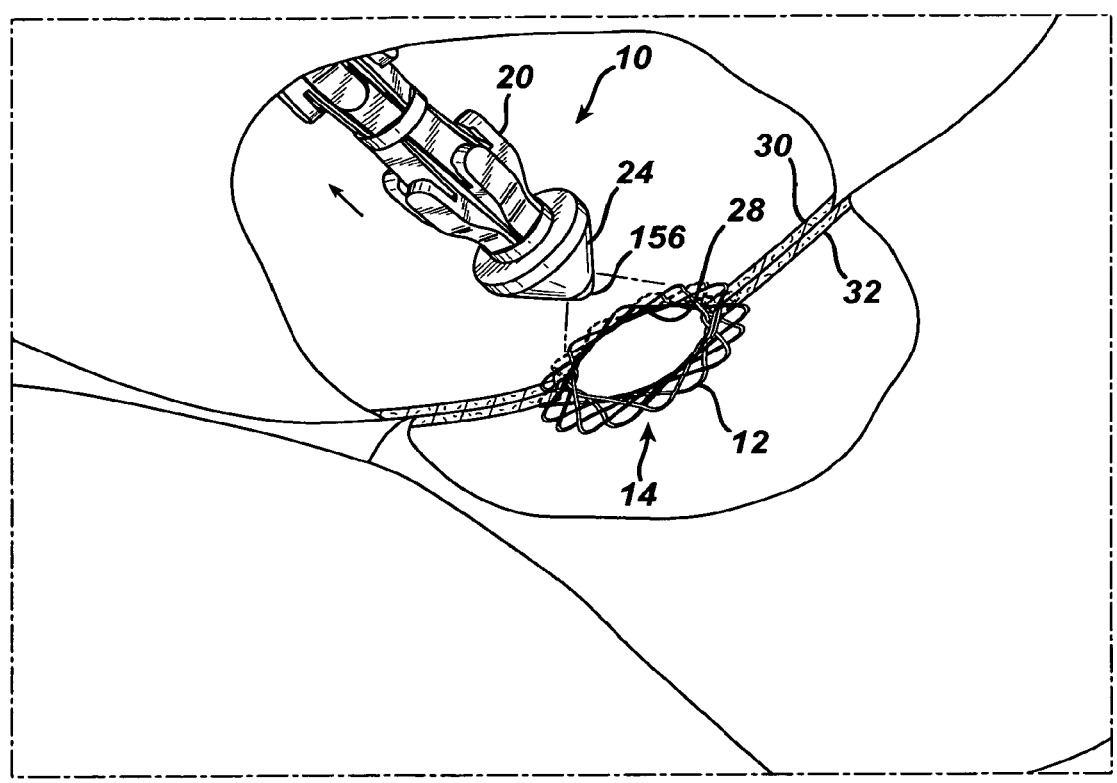
FIG. 11 is a detail perspective view of the distal portion of the applier returned to unactuated state and withdrawn proximally to deploy the actuated anastomotic ring device.
Figure 12:
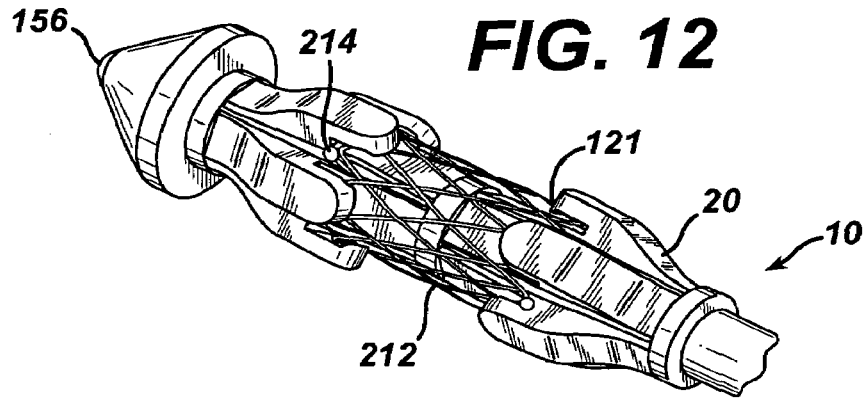
FIG. 12 is a detail perspective view of the distal portion of the applier of FIG. 1 in an unactuated position holding an anastomotic ring device advantageously fabricated with a ball end discontinuous weave.
Figure 13:
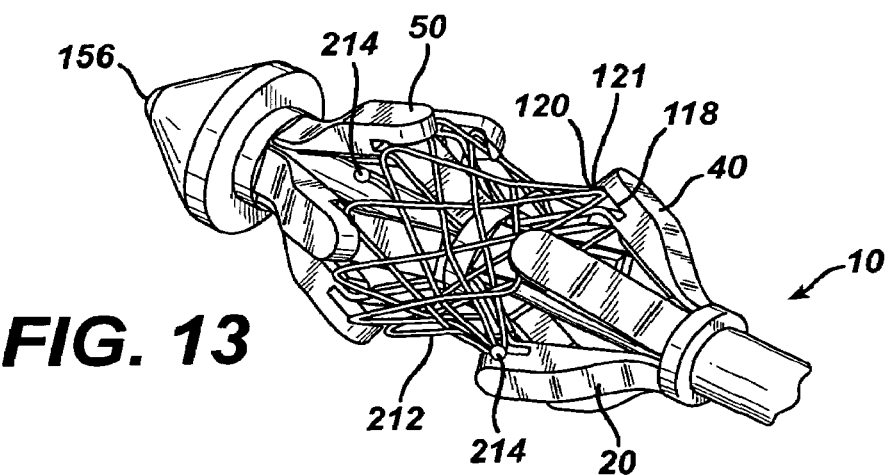
FIG. 13 is a detail perspective view of the distal portion of the applier of FIG. 12 in a partially actuated position.
Figure 14:
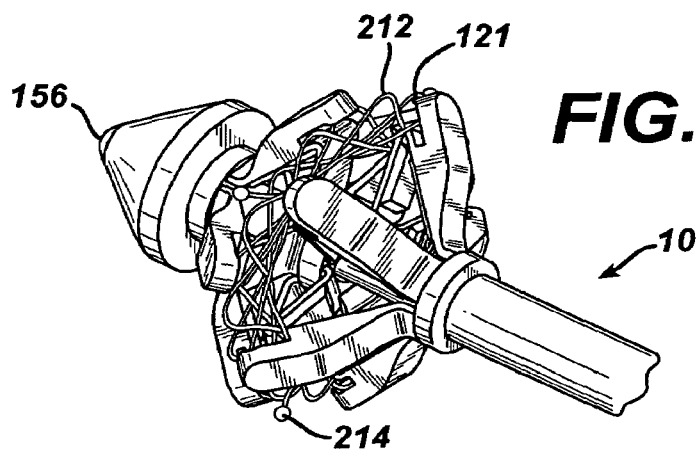
FIG. 14 is a detail perspective view of the distal portion of the applier of FIG. 12 in a fully actuated position.
Figure 15:
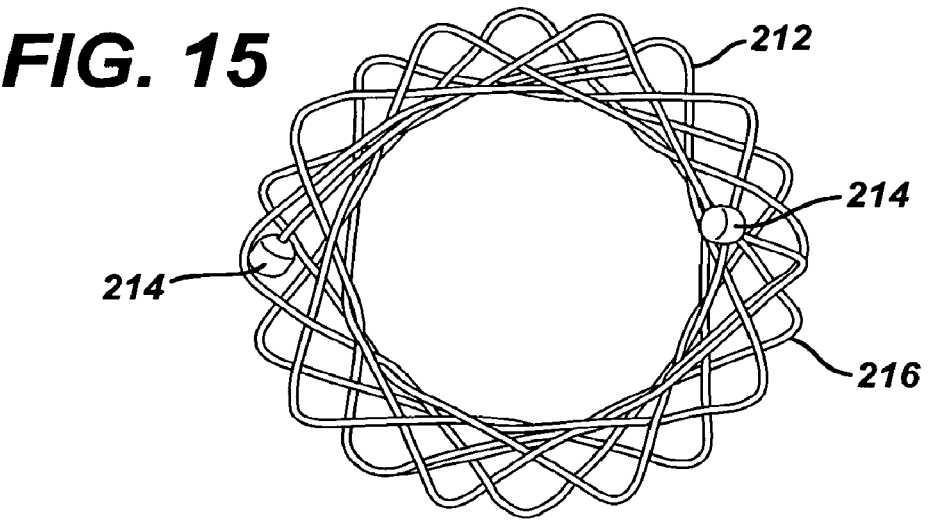
FIG. 15 is an end view of the anastomotic ring device of FIG. 12 after actuation, depicted as a single strand discontinuous weave with a pair of ball ends.
Figure 16:
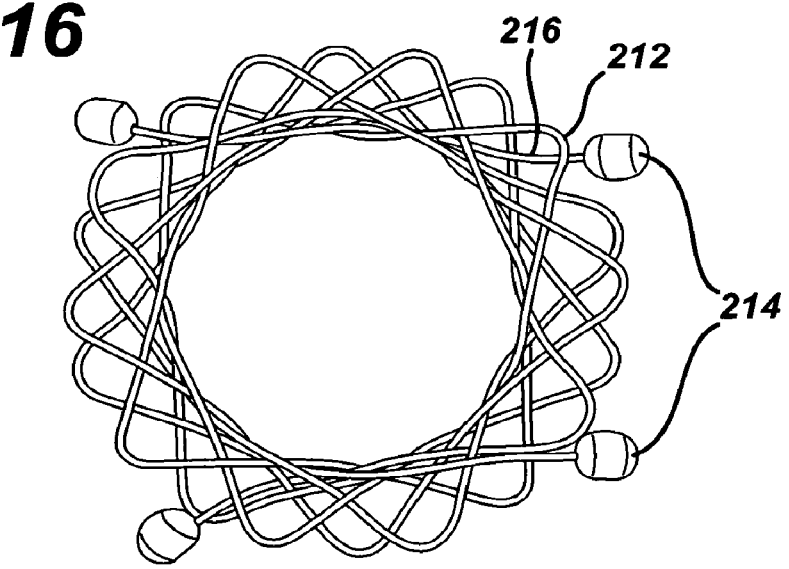
FIG. 16 is an end view of the anastomotic ring device of FIG. 12 after actuation, depicted as a dual strand discontinuous weave, each strand with a pair of ball ends.

In use, the tapered tip 24 of the applier 10 is inserted through a trocar port into a tissue passage that has been placed proximate to another tissue passage that are to be anastomotically joined (See FIGS. 1-2). The tapered tip 24 and a distal half of the molded actuating member 20 and anastomotic ring device 12 are inserted through an anastomotic opening 28 formed therebetween and then the applier is actuated, with a partially actuated applier 10 being depicted in FIGS. 7-8. With particular reference to FIG. 8, the proximal and distal leaves 40, 50 are shown as having gripping slots 118 that grip respective petals 120 of the anastomotic ring device 12, especially in its unactuated, generally cylindrical shape. An inwardly directed retention tip 121 or other gripping features in the gripping slots 118 may be incorporated to enhance retention. These gripping slots 118 assist in preventing the anastomotic ring device 12 from slipping off of the applier 10 or being inappropriately placed thereon for actuation. In FIGS. 9-10, the applier 10 has been fully actuated, forming the anastomotic ring device 12 into a hollow rivet shape to form the anastomotic attachment between tissue walls 30, 32. The fully actuated proximal and distal leaves 40, 50 cause the petals 120 to disengage from the gripping slots 118. Thereafter, the applier 10 is returned to an unactuated condition and the actuated anastomotic ring device 12 deployed by withdrawing the tapered tip 24 from the anastomotic opening 28 and ring device 12, as depicted in FIG. 11.

Deployment Illumination.

Figure 7:
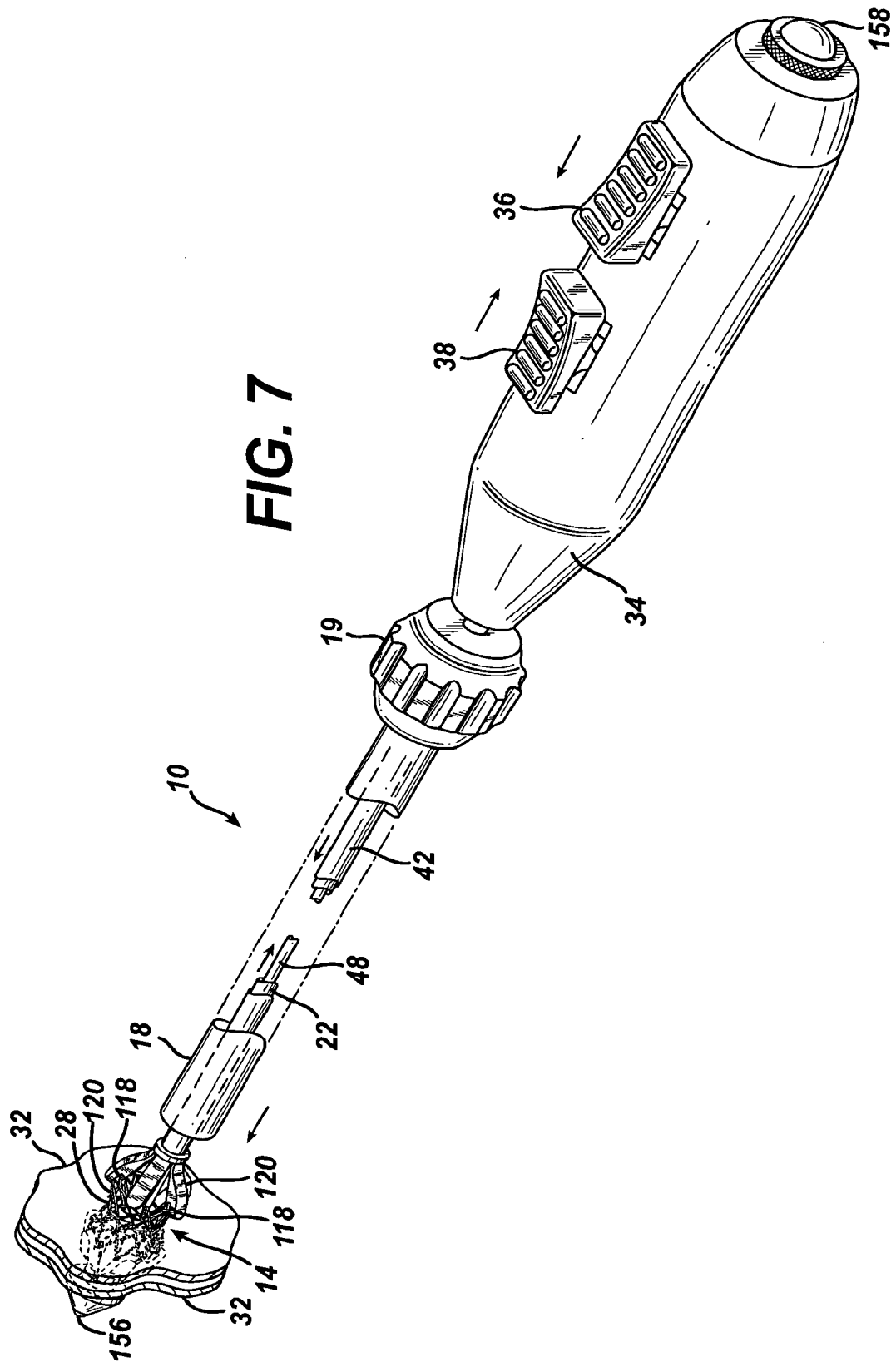
FIG. 7 is a perspective view of the applier of FIG. 1 in a partially actuated state.

In FIGS. 7, 9, a distal portion of the anastomotic ring device 12 are depicted in phantom to illustrate their actuated position. This phantom depiction is also suggestive of a clinical advantage of being able to view the deployment condition from a proximal point of view. Typically, an endoscope will view the anastomotic opening 28 from a proximal position. Returning to FIGS. 2-7, adding a deployment illumination feature to the applier 10 provides this ability to view deployment through translucent tissue walls. Specifically, an illumination power source (e.g., battery) 150 and control (e.g., switch) 152 are incorporated into the handle 34 with a conductor, depicted as a twisted wire pair 154 passing through the internal rod 48 to the tapered tip 24, which includes a proximally directed electroluminescence device 156. Alternatively conductive ink traces may be applied longitudinally down portions of the applier 10 to provide an electrical circuit to the tapered tip 24. An externally accessible push button 158 drives the power source 150 against the control 152, creating an illumination circuit with the electroluminescence device 156.

Alternatively or in addition, the molded actuating member 20 may be formed of a fluorescent or electroluminescent material that is either stimulated prior to insertion or receives light from a light source of the applier 10.

Discontinuous Weave Anastomotic Ring Device.

Figure 17:
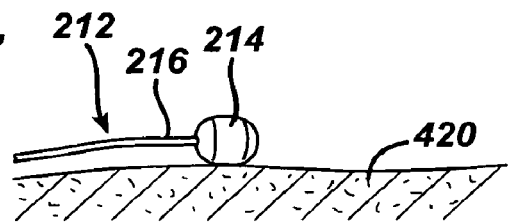
FIG. 17 is a detail view of a ball end of the anastomotic ring device of FIG. 12 in atraumatic contact with a tissue wall.
Figure 18:
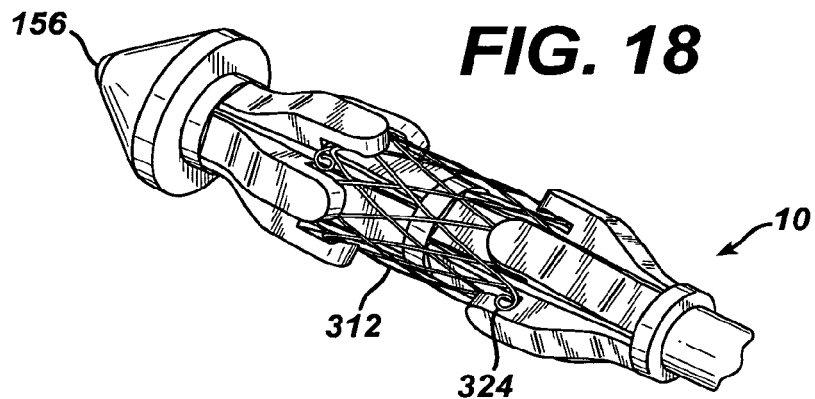
FIG. 18 is a detail perspective view of the distal portion of the applier of FIG. 1 in an unactuated position holding an anastomotic ring device advantageously fabricated with a loop end discontinuous weave.
Figure 19:
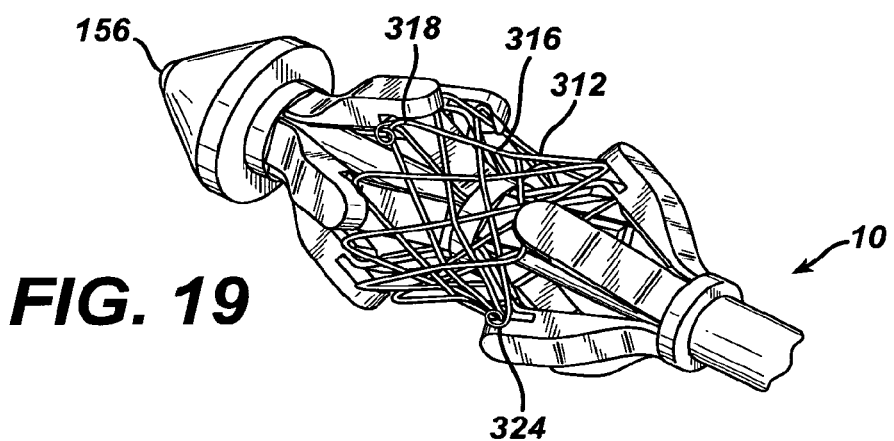
FIG. 19 is a detail perspective view of the distal portion of the applier of FIG. 18 in a partially actuated position.
Figure 20:
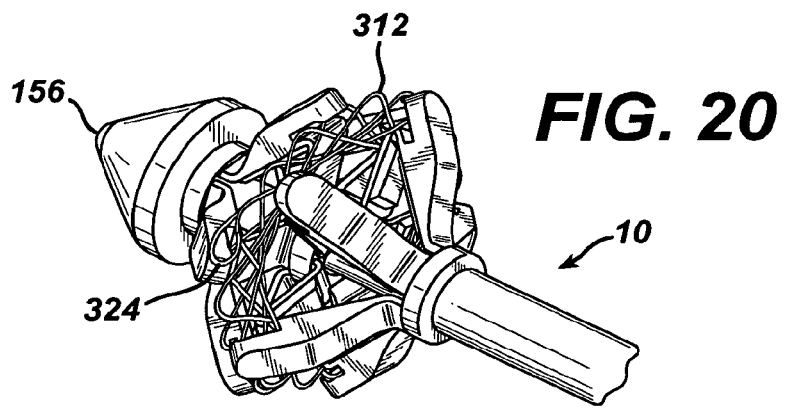
FIG. 20 is a detail perspective view of the distal portion of the applier of FIG. 18 in a fully actuated position.
Figure 21:
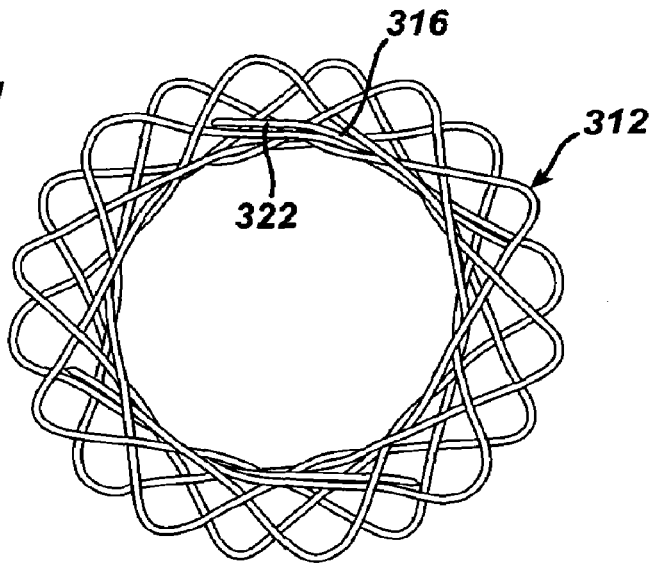
FIG. 21 is an end view of an anastomotic ring device after actuation, depicted as a dual strand discontinuous weave each strand with straight ends.
Figure 22:
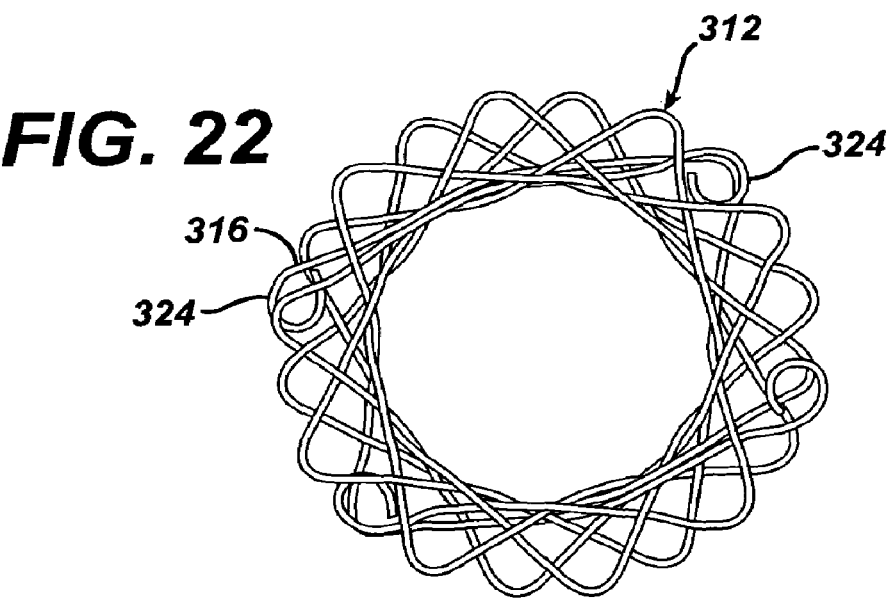
FIG. 22 is an end view of the anastomotic ring device of FIG. 18 after actuation, depicted as a dual strand discontinuous weave, each strand with a pair of loop ends.
Figure 23:
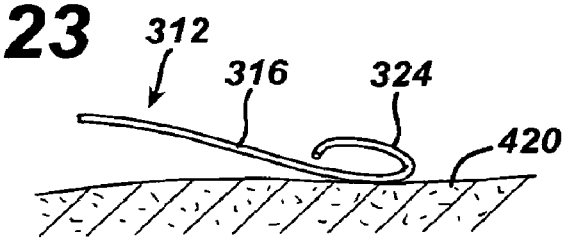
FIG. 23 is a detail view of a loop end of the anastomotic ring device of FIG. 18 in atraumatic contact with a tissue wall.
Figure 24:
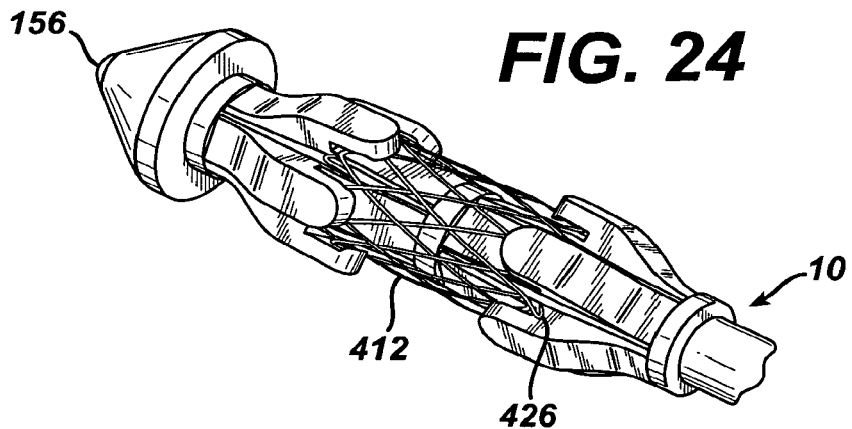
FIG. 24 is a detail perspective view of the distal portion of the applier of FIG. 1 in an unactuated position holding an anastomotic ring device advantageously fabricated with a hook end discontinuous weave.
Figure 25:
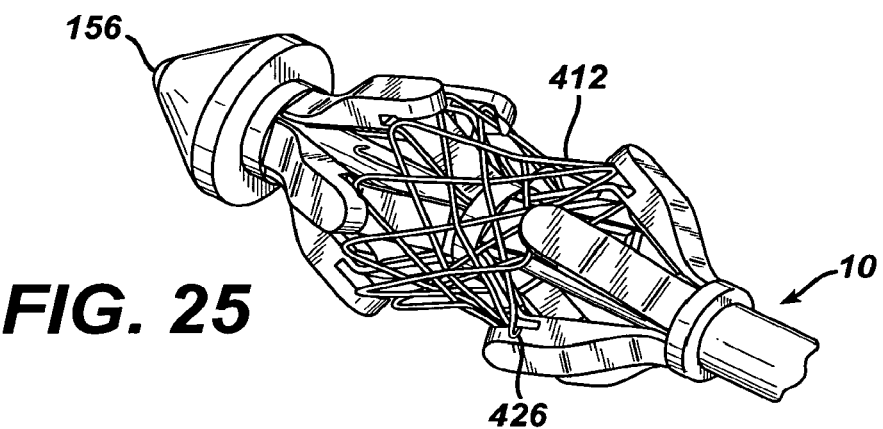
FIG. 25 is a detail perspective view of the distal portion of the applier of FIG. 24 in a partially actuated position.
Figure 26:
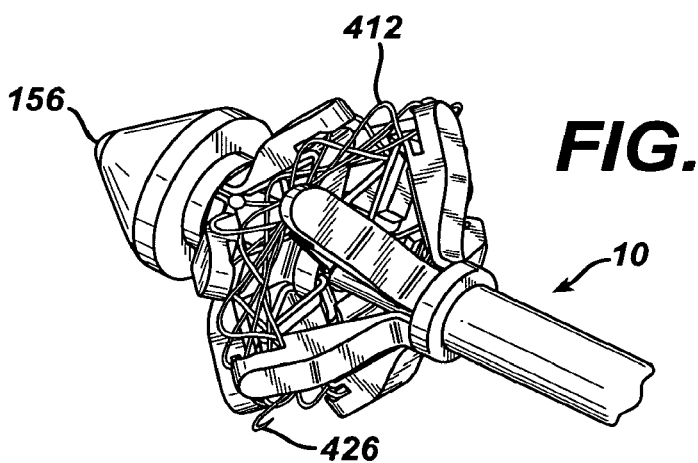
FIG. 26 is a detail perspective view of the distal portion of the applier of FIG. 24 in a fully actuated position.
Figure 27:
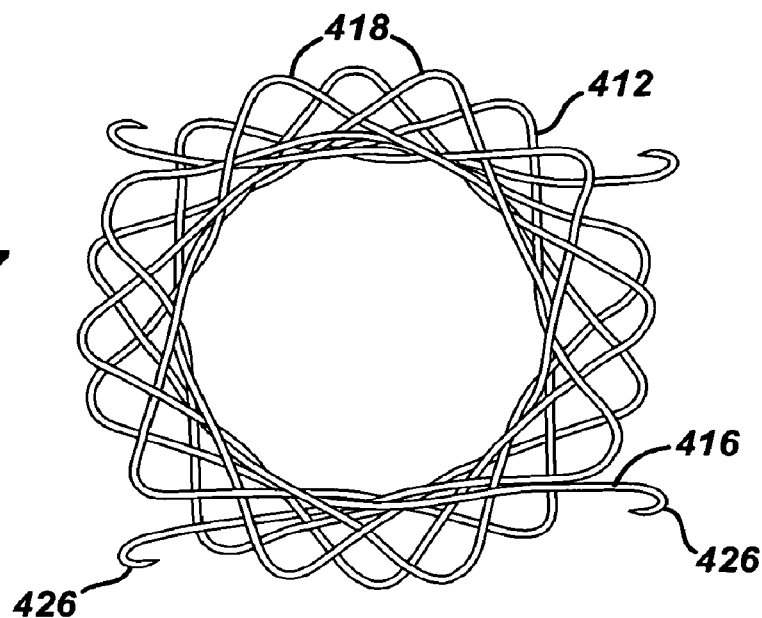
FIG. 27 is an end view of an anastomotic ring device after actuation, depicted as a dual strand discontinuous weave each strand with a pair of hook ends.
Figure 28:
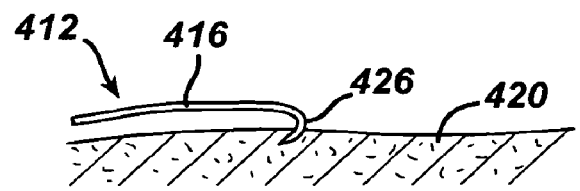
FIG. 28 is a detail view of a loop end of the anastomotic ring device of FIG. 24 in traumatic contact with a tissue wall.

Forming an anastomotic ring device with a continuous wire loop poses a difficult manufacturing process that includes joining the ends of the woven wire strand or forming a weave from a continuous wire loop. In FIGS. 12-17 an advantageous approach to fabricating an anastomotic ring device 212 includes adding ball ends 214 to each wire strand 216. In an illustrative embodiment, a hole is laser formed in each ball end 214 and then the ball end 214 is crimped onto the wire strand 216. The ball ends 214 assist in preventing unraveling of petals 218 formed by the woven strands 216. In addition, the ball ends 214 form an atraumatic contact with a tissue wall 220, as depicted in FIG. 17.

As an alternative discontinuous weave, an anastomotic ring device 312 in FIGS. 18-23 is formed by one or more wire strands 316 whose ends are not attached to one another but instead positioned within the confines of petals 318 of the anastomotic ring device 312. Specifically, in FIG. 21, each strand 316 terminates in a generally straight end 322. In FIGS. 18-20, 22-23, each strand terminates in a loop end 324. In each instance, positioning each end 322, 324 within petals 318 of the anastomotic ring device 312 avoids interference with an applier while also simplifying manufacturer.

As yet a further alternative discontinuous weave, an anastomotic ring device 412 in FIGS. 24-28 is formed by one or more wire strands 416 whose ends are not attached to one another but instead are positioned outside of petals 418 of the woven strands 416. In a depicted version, each strand 416 traumatically engages a tissue wall 420 with hook ends 426 interdigitated between the petals 416.

Spring Closed Ring Anastomotic Device.

Figure 29:
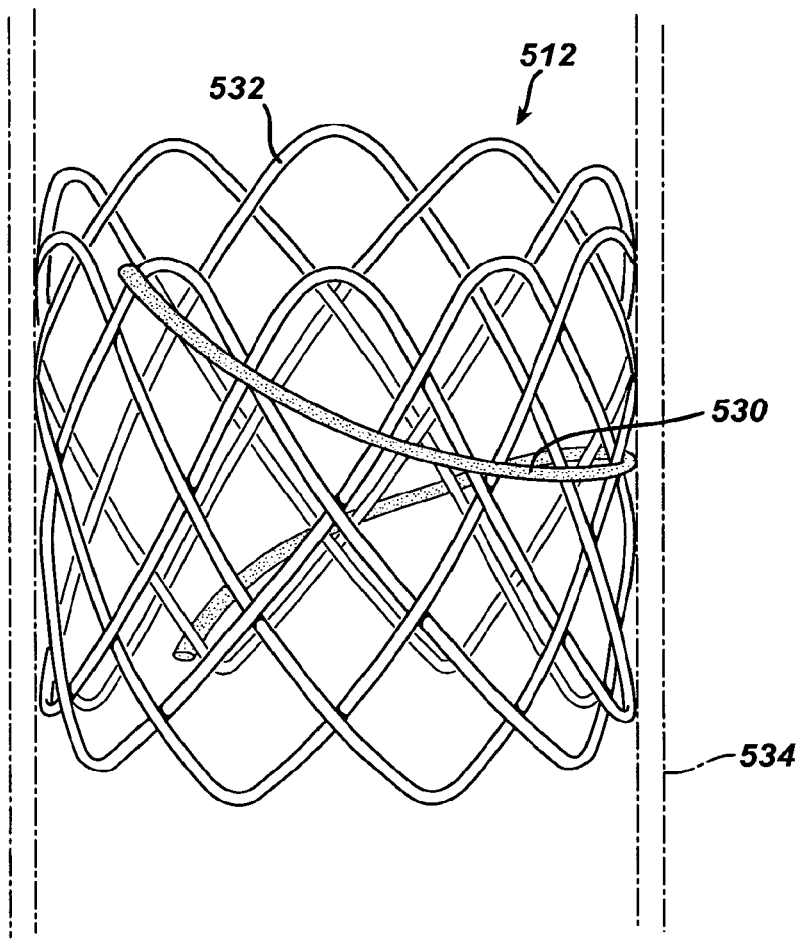
FIG. 29 is a side view of an anastomotic ring device including a helical actuation coil and constrained within a sheath.
Figure 30:
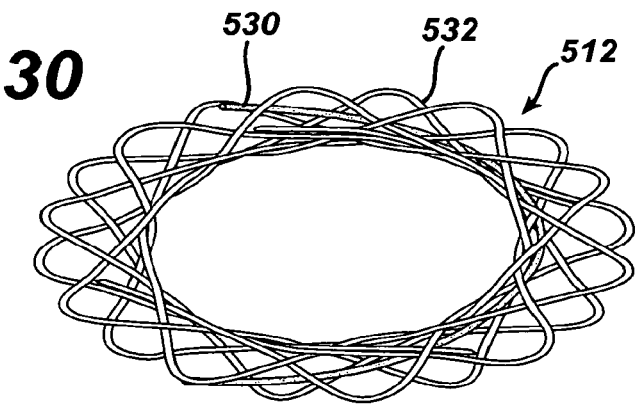
FIG. 30 is a perspective view of the anastomotic ring device of FIG. 30 in an actuated condition.

In FIGS. 29-30, an anastomotic ring device 512 includes a helical wire assist spring 530 fabricated from an SME material (e.g., nitinol) or from spring steel. Thus, the woven material of a stent portion 532 of the anastomotic ring device 512 need not be of an SME material, or at least need not rely entirely upon its SME properties to effect actuation. The helical wire assist spring 530 enables selection of a stent portion 532 of a desired wire thickness and of a desired material. For instance, the stent portion 532 may even be of plastic or longitudinally cut discrete sections of a continuously woven wire braid that provide no inherent actuating capability.

In FIG. 29, the wire assisted anastomotic ring device 512 is depicted in a generally cylindrical shape constrained by a lumen 534, which may be an applier. It will be appreciated that the wire assisted anastomotic ring device 512 may advantageously be implanted by use of the applier 10 described above, which would advantageously affirmatively grip the wire assisted anastomotic ring device to hold it in the stressed, unactuated position prior to implantation.

Deflected Petal Anastomotic Ring Device.

Figure 31:
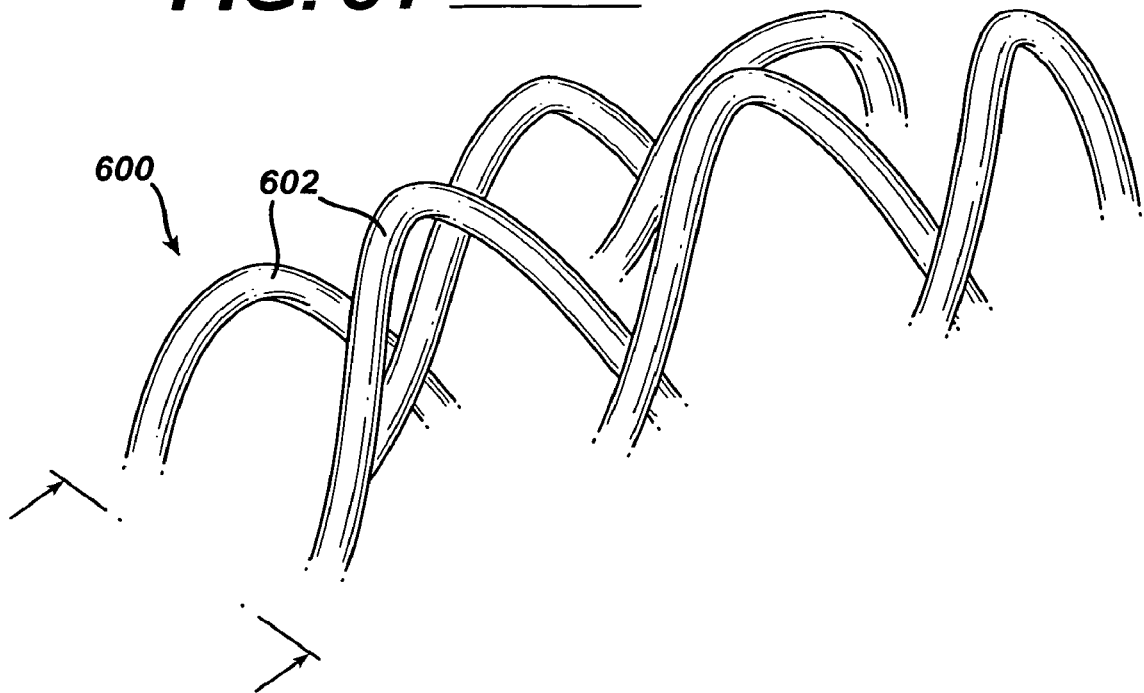
FIG. 31 is a side view of a generally known anastomotic ring having converging distal petals.
Figure 32:
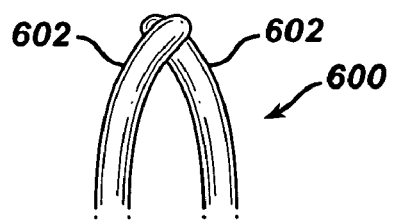
FIG. 32 is a detail view of the generally-known anastomotic ring of FIG. 31.

The generally-known nitinol ring device 600 includes converging looped petals 602 whose distal end flare lateral to the longitudinal axis when viewed in their stressed, generally cylindrical state, and interdigitate when viewed in their relaxed, actuated state, as depicted in FIGS. 31-32. It is believed that such deflected petals 602 engage the tissue walls in a beneficial fashion. However, the resulting increase in outward slope of each petal 602 imposes an increasing amount of friction to self-actuation of the generally-known nitinol ring device 600, negating any advantage of engagement, requiring more force to self-deploy generally-known nitinol ring device 600.

As generally-known nitinol ring device 600 deploys, portions of wire forming generally-known nitinol ring device 600 move relative to each other while in contact. The curvature of the wire winding of generally-known nitinol ring device 600 forms local maxima and minima for a contacting wire to traverse. The converging looped petals cause a local minimum for a contacting wire portion that the contacting wire portion must overcome. An increasing force gradient opposing deployment occurs, and must be overcome by the internal stored energy of the generally-known nitinol ring device 600 to complete deployment.

Figure 33:
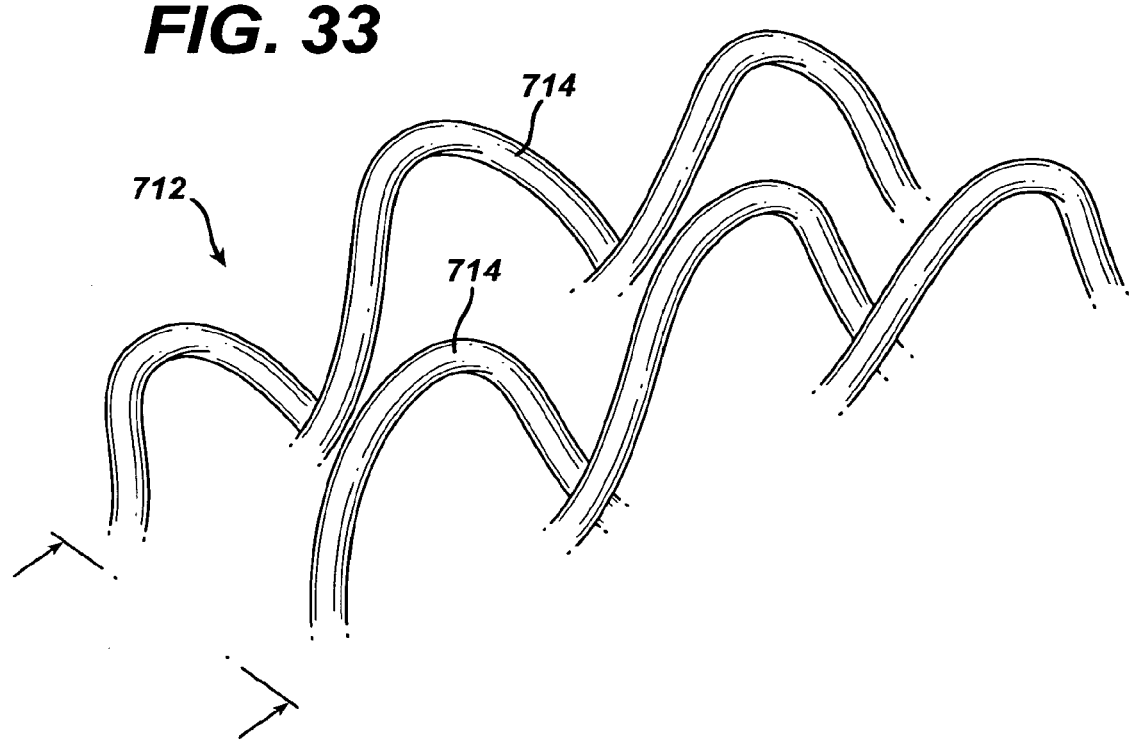
FIG. 33 is a perspective view of an anastomotic ring device incorporating diverging petals.
Figure 34:
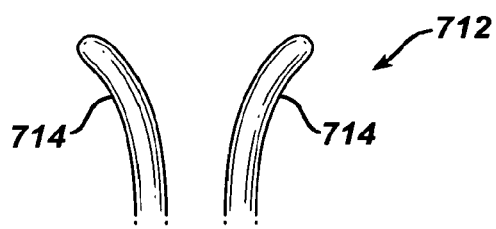
FIG. 34 is a side detail view of the diverging petals of the anastomotic ring device of FIG. 33.

In FIGS. 33-34, an anastomotic ring device 712 advantageously includes distal looped petals 714 that are divergent (flared away) from each other when the ring device 712 is in its relaxed, hollow rivet (ring) shape as depicted. It is further believed that deflecting the distal portions of each petal 714 away from the tissue walls may decrease excessive pressure at the anastomotic attachment site without significant degradation to its required amount of attachment forces. Moreover, for anastomotic ring devices 712 that are not formed of an absorbable material, this configuration may advantageously later more readily detach after the anastomotic attachment is permanently formed between tissue walls.

Anastomotic ring device 712, with divergent (flared away) petals, will a cause a maximum in force tending to urge the anastomotic ring device 712 towards the actuated ring state.

Figure 35:
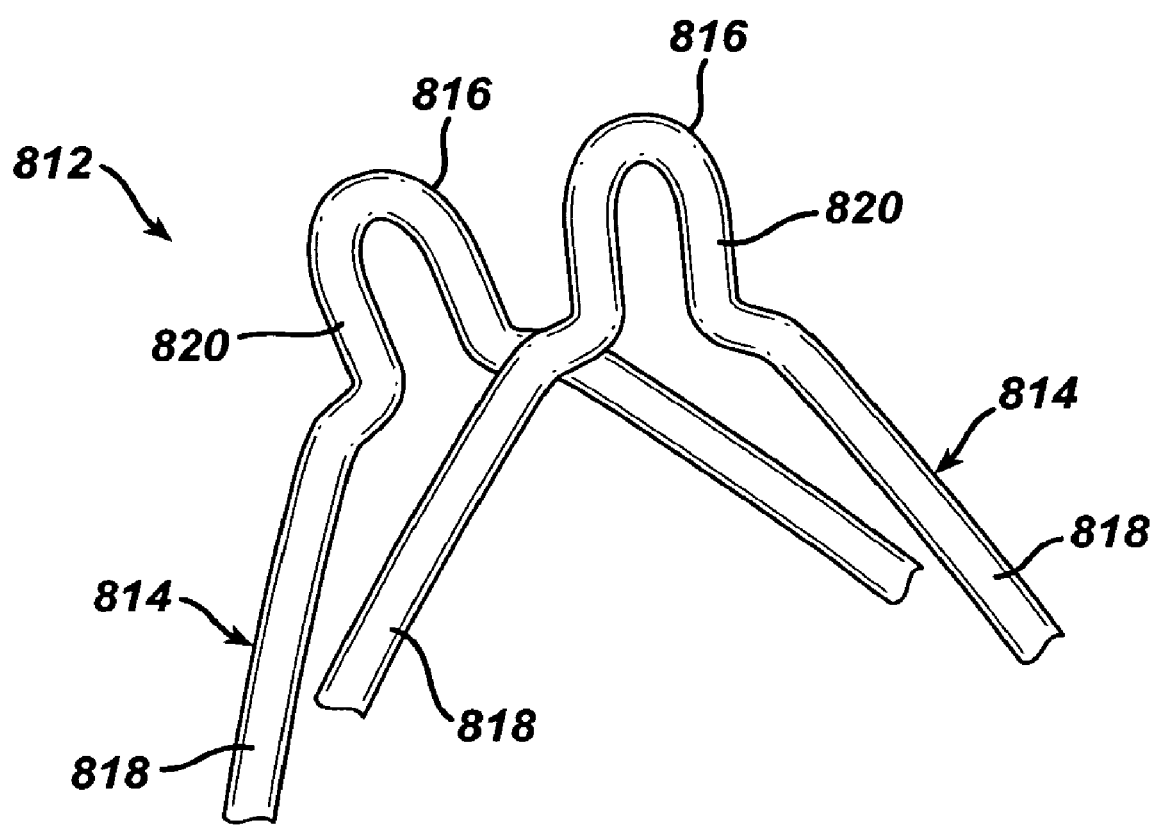
FIG. 35 is side view of two arcuate members with a reduced radius point for an anastomotic ring device.

With reference to FIG. 35, an anastomotic ring device 812 includes petals 814 whose distal portion 816 is formed with a small radius relative to its more proximal portions 818 that overlap each other and slide across each other during actuation. As depicted, straight portions 820 between the distal and proximal portions 816, 818 may be shaped such that in the stressed, cylindrical shape of the ring device 812 that the petals 814 are urged toward the actuated ring state.

It should be appreciated that the divergent position of the petals may further be enhanced by SME treatment of these distal portions wherein the stressed, generally cylindrical state of the ring device 814 may include a straight petal or even a converging petal for purposes such as enhancing user of an applier 10 and/or achieving a good anastomotic attachment immediately upon actuation with an eventual steady-state actuation position being as depicted.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, although bariatric procedures for bypassing portions of a gastrointestinal tract are depicted, it should be appreciated that other surgical procedures may benefit by an anastomotic ring device having aspects described herein.

For another example, although an applier 10 has been advantageously depicted that assists in actuating the anastomotic ring device 10, it should be appreciated that the anastomotic ring device 10 includes enhanced reliability and performance in self-actuating and thus may be inserted by other means, to include insertion through the opening and released without the application of an external actuating force.

For yet a further example, various improvements disclosed herein may be used in various combinations.

What is claimed is:

1. An anastomotic device comprising a slidingly woven tube, the woven tube defining a longitudinal axis and having each longitudinal end terminate in slidably engaging circumferential petals, the woven tube having an unactuated position of a generally cylindrical shape and an actuated position of a hollow rivet shape respectively for insertion through and for forming an anastomotic attachment defining a hollow opening between two proximate tissue walls at an anastomotic surgical site, wherein each petal comprises a petal tip flaring directionally outward away from the tissue walls when the anastomotic device is in the actuated position, and as said anastomotic device moves from the unactuated to the actuated position, the direction of the flare reduces sliding friction between moving petals, and when the anastomotic device is in the actuated position, the direction of the flare away from the tissue walls reduces pressure on tissue captured between the tip of each petal, wherein the woven tube comprises two strands, each strand of the two strands having unattached ends, wherein the unattached ends are flared in the same direction as the petal tips, wherein the petal tips are formed by bent portions of the wire strands such that each wire strand extends away from a respective first petal tip to form respective second and third petal tips after bending to form the respective first petal tip, wherein the unattached ends each terminate in a respective loop, wherein the loops are configured to position the unattached ends away from tissue contact when the anastomotic device is in the deployed position.

2. The anastomotic device of claim 1, wherein an underlying portion of each circumferential petal is shaped to diverge from an overlying portion of an adjacent petal for mitigating resistance to actuation.

3. The anastomosis device of claim 1, wherein the flaring of each circumferential petal tip comprises a monotonic slope toward a distal tip of the petal.

4. The anastomotic device of claim 1, wherein at least a portion of each petal has an uncurved section.

5. The anastomotic device of claim 1, wherein the unattached end of each loop is positioned adjacent to another portion of the loop to shield the unattached end from tissue contact.

6. The anastomotic device of claim 1, wherein the unattached ends extend outside of the woven petals.

7. The anastomotic device of claim 1, wherein the anastomotic device is configured to operably engage with an anastomotic device applier and the unattached ends are configured to avoid interference with the applier when moving the anastomotic device from the unactuated to the actuated position.

8. The anastomotic device of claim 1, wherein the wire has shape memory effect properties.

* * * * *